(12) United States Patent
Sa et al.

(10) Patent No.: US 11,389,665 B2
(45) Date of Patent: Jul. 19, 2022

(54) CAPSULE TYPE PHOTODYNAMIC THERAPY APPARATUS WITH ANCHOR

(71) Applicant: KOREA PHOTONICS TECHNOLOGY INSTITUTE, Gwangju (KR)

(72) Inventors: GiDong Sa, Gwangju (KR); Ja-Yeon Kim, Gwangju (KR); Sun-Hee Ahn, Gwangju (KR); JinYoung An, Gwangju (KR); Sa-Ung Kim, Gwangju (KR); EunBee Kim, Gwangju (KR); Ji-Ho Jeong, Jeonju-si (KR)

(73) Assignee: KOREA PHOTONICS TECHNOLOGY INSTITUTE, Gwangju (KR)

( * ) Notice: Subject to any disclaimer, the term of this patent is extended or adjusted under 35 U.S.C. 154(b) by 205 days.

(21) Appl. No.: 16/685,360

(22) Filed: Nov. 15, 2019

(65) Prior Publication Data
US 2021/0128933 A1    May 6, 2021

(30) Foreign Application Priority Data
Oct. 30, 2019  (KR) .................... 10-2019-0136371

(51) Int. Cl.
*A61N 5/06*    (2006.01)
(52) U.S. Cl.
CPC ......... *A61N 5/062* (2013.01); *A61N 5/0601* (2013.01); *A61N 2005/0632* (2013.01); *A61N 2005/0664* (2013.01)

(58) Field of Classification Search
CPC .................. A61N 5/0601; A61N 5/062
USPC ............................................. 600/302
See application file for complete search history.

(56) References Cited

U.S. PATENT DOCUMENTS

| | | | |
|---|---|---|---|
| 2008/0068453 A1* | 3/2008 | Mori ............. | A61B 1/041 348/65 |
| 2010/0121420 A1* | 5/2010 | Fiset ............ | A61N 5/06 607/94 |
| 2012/0226335 A1* | 9/2012 | Surrenti ........ | A61N 5/0603 607/89 |
| 2013/0013031 A1* | 1/2013 | Ben-Yehuda .... | A61B 5/073 607/92 |
| 2020/0114171 A1* | 4/2020 | Tortora ......... | A61B 5/4238 |

FOREIGN PATENT DOCUMENTS

| | | | | |
|---|---|---|---|---|
| JP | 2019-130166 A | | 8/2019 | |
| JP | 2019130166 A | * | 8/2019 | ........... A61N 5/06 |
| KR | 10-2003-0039221 A | | 5/2003 | |
| KR | 10-0996487 B1 | | 11/2010 | |
| KR | 10-0998722 B1 | | 12/2010 | |
| KR | 100998722 B1 | * | 12/2010 | ........... A61N 5/06 |
| KR | 10-1441792 B1 | | 9/2014 | |
| WO | 2018/144594 A1 | | 8/2018 | |

* cited by examiner

*Primary Examiner* — Nathan J Jenness
(74) *Attorney, Agent, or Firm* — Studebaker & Brackett PC

(57) ABSTRACT

Disclosed herein is a capsule type photodynamic therapy apparatus. The apparatus has an anchor packaged with a silicone dome to anchor the apparatus to target tissue in a body by an endoscope, and includes a battery to communicate with an external device via human body communication in the silicone dome, and is repeatedly operated several times under the control of the external device to irradiate the target tissue with a therapeutic light source and thereby repeatedly treat the target tissue several times.

6 Claims, 4 Drawing Sheets

CAPSULE TYPE PHOTODYNAMIC THERAPY APPARATUS WITH ANCHOR

CROSS REFERENCE TO RELATED APPLICATION

The present application claims priority to Korean Patent Application No. 10-2019-0136371, filed Oct. 30, 2019, the entire contents of which are incorporated herein for all purposes by this reference.

BACKGROUND OF THE INVENTION

Field of the Invention

The present invention relates to a capsule type photodynamic therapy apparatus. More particularly, the invention relates to a capsule type photodynamic therapy apparatus, which has an anchor packaged with a silicone dome to anchor the apparatus to target tissue in a body by an endoscope, and irradiates the target tissue in the silicone dome with therapeutic light source to treat the target tissue.

Description of the Related Art

A death rate caused by a malignant tumor, such as cancer, continues to increase. Thus, various methods for treating malignant tumors are being studied.

Generally, systemic anticancer therapy and radiation treatment are mainly used as the method for treating malignant tumors. However, systemic anticancer therapy and radiation treatment can only be performed a limited number of times due to side effects of the treatment.

Thus, there is a need to develop a treatment method that reduces the risk of patients, has fewer side effects, and is applied in combination with the systemic anticancer therapy and the radiation treatment.

To satisfy such a need, a targeted photodynamic therapy technique, which may be applied in combination with the systemic anticancer therapy and the radiation treatment, reduces a tumor extent before performing endoscope resection, and allows minimal resection when necessary, is being studied.

As the targeted photodynamic therapy technique, photodynamic therapy using a laser probe is applied.

However, the photodynamic therapy using the laser probe is problematic in that the probe may be broken and output is limited due to optical loss.

DOCUMENTS OF RELATED ART (Patent Document 1) KR Patent No. 10-1441792 (published on Sep. 17, 2014)

SUMMARY OF THE INVENTION

The present invention has been made in order to solve the above-mentioned problems in the prior art and an object of the present disclosure is to provide a capsule type photodynamic therapy apparatus, which has an anchor packaged with a silicone dome to anchor the apparatus to target tissue in a body by an endoscope, and irradiates the target tissue in the silicone dome with therapeutic light source to treat the target tissue, thus solving a problem caused by a broken laser probe and a problem where output is limited due to optical loss.

In order to achieve the object of the present invention, the invention provides a capsule type photodynamic therapy apparatus with an anchor, the apparatus including a capsule body having the anchor that protrudes outwards to be anchored to a target tissue in a body; a board unit coupled to an inside of an upper portion of the capsule body; a light irradiation unit electrically coupled to an upper portion of the board unit to be formed long in a longitudinal direction, radiating light in at least both directions, and including at least one micro-light source provided longitudinally in the at least both directions; and a silicone dome transmitting light radiated from the light irradiation unit, configured to have a shape of a cap that is opened at a side thereof to cover the light irradiation unit and the board unit, and coupled to the upper portion of the capsule body while covering the light irradiation unit and the board unit, thus packaging the capsule body, the light irradiation unit, and the board unit.

The capsule body may include a cylindrical capsule body; a cap coupler provided on the upper portion of the capsule body so that the silicone dome is coupled to the upper portion; a double packing extending from the cap coupler to have an inner radius smaller than that of the cap coupler, with a protrusion being doubly formed along an outer circumference thereof; and at least one anchor protruding outwards below the cap coupler of the capsule body, and pointed at an end thereof to be fixedly inserted into the target tissue, wherein the silicone dome may include a cap body transmitting light irradiated from the light irradiation unit, configured to have a shape of a cap that is opened at a side thereof to cover the light irradiation unit and the board unit, and coupled to the upper portion of the capsule body while covering the light irradiation unit and the board unit; and a double packing coupler provided in the cap body corresponding to the double packing, and doubly coupled with the double packing to doubly package the light irradiation unit and the board unit.

The anchor may protrude to form an oblique line with an outer circumference of the capsule body within a predetermined angle.

The light irradiation unit may include at least two micro-light sources provided to radiate light; a flexible film formed long in a longitudinal direction, each of the micro-light sources being longitudinally connected to the flexible film to radiate light in at least both directions; and a board connector provided on an end of the flexible film, connected electrically to the micro-light source, and coupled electrically to an upper portion of the board unit.

The flexible film may include the micro-light source on only one of both surfaces, and be bent so that the micro-light source radiates light in both directions, and the board connector may be provided on each of both ends of the flexible film.

The flexible film may include at least three micro-light sources on only one of both surfaces, and be bent so that the micro-light source radiates light in both directions and in a direction perpendicular to the both directions, and the board connector may be provided on each of both ends of the bent flexible film.

The capsule body may further include a space defining an empty space therein; and a battery inserted into the space, and connected electrically to the board unit to supply power to the board unit and the light irradiation unit.

The present invention provides a capsule type photodynamic therapy apparatus, which may be used for treatment in combination with radiation treatment and systemic anticancer treatment, and has no side effect, thus treating a target tissue in a body without limit on number of treatments.

Furthermore, the present invention provides a capsule type photodynamic therapy apparatus, which is inserted into a target tissue in a body to treat the target tissue, thus preventing a probe from being broken and preventing light output from being limited during surgery.

Moreover, the present invention provides a capsule type photodynamic therapy apparatus, which is provided with an anchor to be anchored to a target tissue, thus continuously retaining the capsule type photodynamic therapy apparatus at an initially inserted location, and thereby allowing the target tissue to be continuously and precisely treated.

Furthermore, the present invention provides a capsule type photodynamic therapy apparatus, which may be removed after treatment, thus increasing patient convenience and treatment effect.

BRIEF DESCRIPTION OF THE DRAWINGS

The above and other objects, features, and other advantages of the present invention will be more clearly understood from the following detailed description when taken in conjunction with the accompanying drawings, in which.

DETAILED DESCRIPTION OF THE INVENTION

Hereinafter, the configuration and operation of a capsule type photodynamic therapy apparatus according to the present invention will be described in detail with reference to the accompanying drawings.

Figure 1:
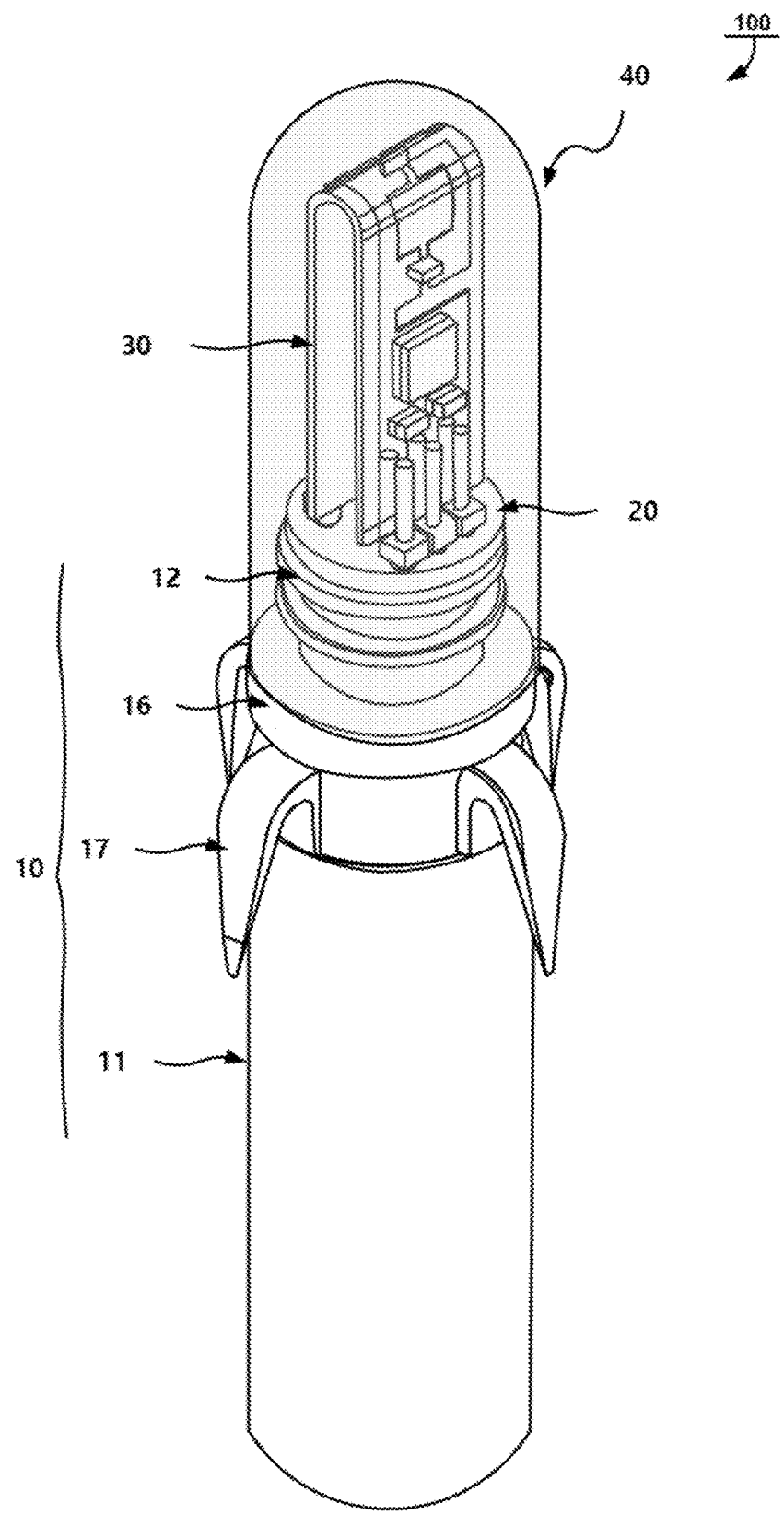
FIG. 1 is a perspective view illustrating a capsule type photodynamic therapy apparatus with an anchor according to the present invention.
Figure 2:
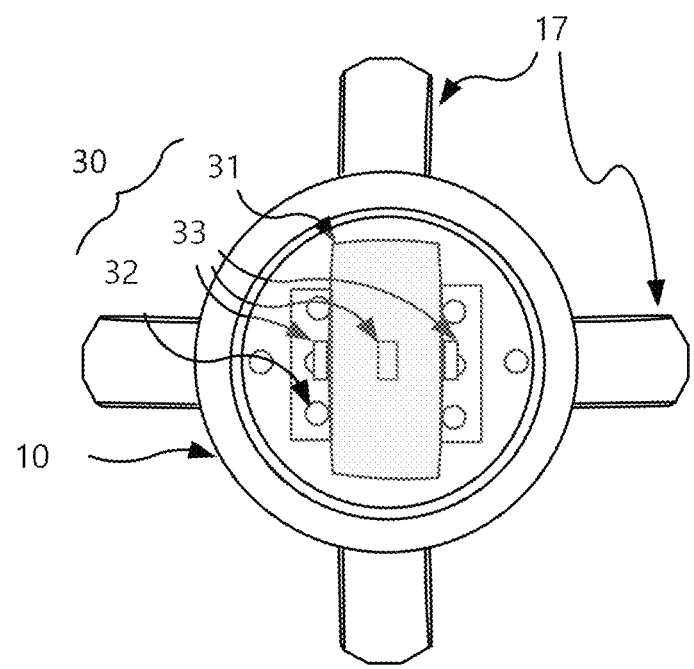
FIG. 2 is a plan view illustrating the capsule type photodynamic therapy apparatus with the anchor according to the present invention.
Figure 3:
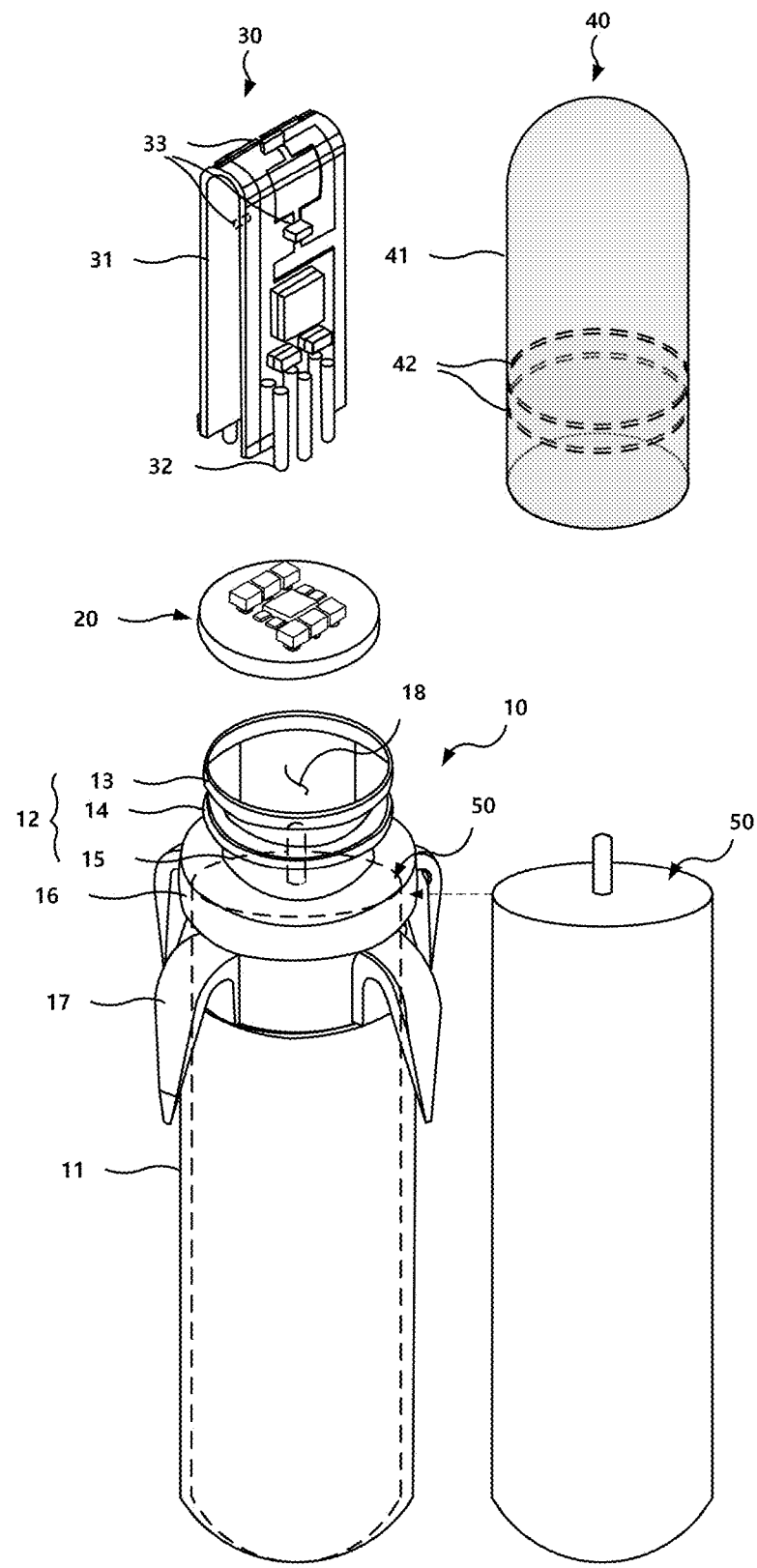
FIG. 3 is an exploded perspective view illustrating the capsule type photodynamic therapy apparatus with the anchor according to the present invention.
Figure 4:
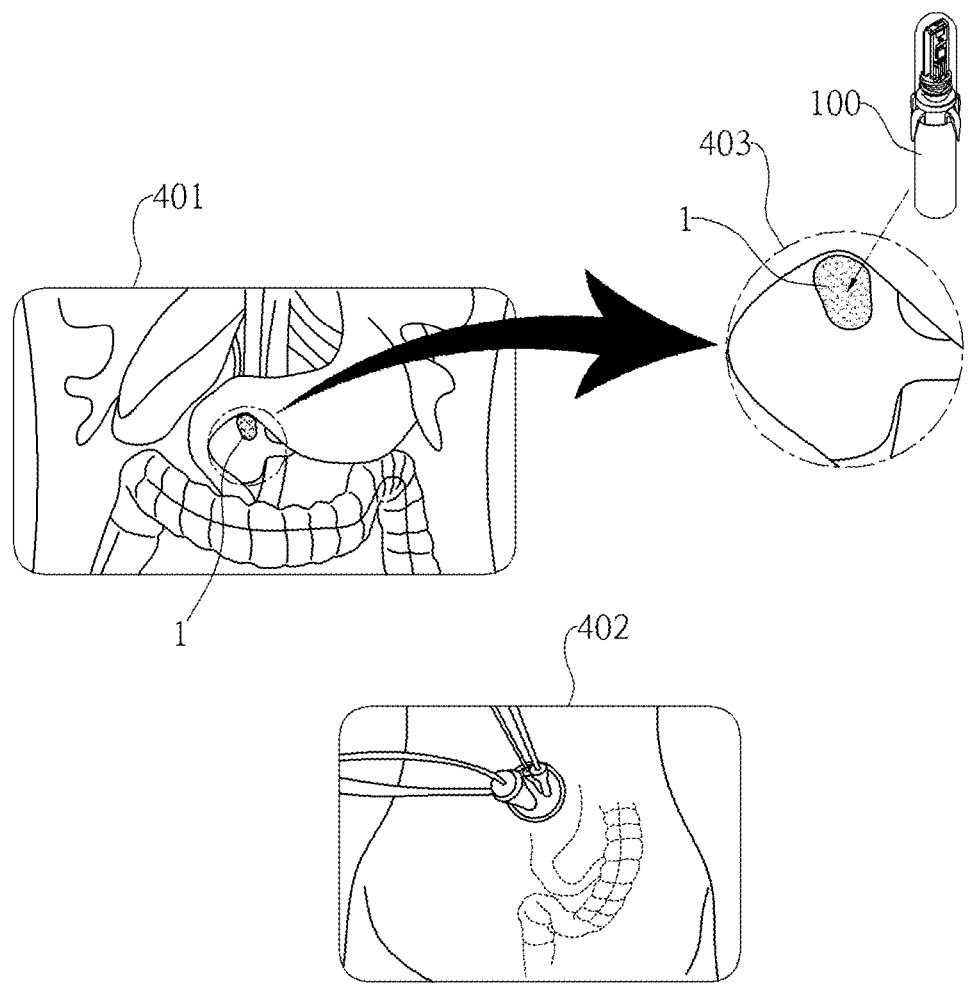
FIG. 4 is a schematic view illustrating an example where the capsule type photodynamic therapy apparatus with the anchor according to the present invention is inserted into a target tissue.

FIG. 1 is a perspective view illustrating a capsule type photodynamic therapy apparatus with an anchor according to the present invention, FIG. 2 is a plan view illustrating the capsule type photodynamic therapy apparatus with the anchor according to the present invention, FIG. 3 is an exploded perspective view illustrating the capsule type photodynamic therapy apparatus with the anchor according to the present invention, and FIG. 4 is a schematic view illustrating an example where the capsule type photodynamic therapy apparatus with the anchor according to the present invention is inserted into target tissue. Hereinafter, the invention will be described with reference to FIGS. 1 to 4.

The capsule type photodynamic therapy apparatus 100 according to the present invention includes a capsule body unit 10, a board unit 20, a light irradiation unit 30, and a silicone dome 40. The apparatus may include a battery 50 according to an embodiment.

The capsule type photodynamic therapy apparatus 100 according to the present invention may be of a capsule structure having the diameter of 2.5 mm, 15 mm, etc. according to the location and size of the target tissue. In order to treat malignant tumors (solid cancer such as liver cancer, cholangiocarcinoma, pancreatic cancer, or colorectal cancer), a second-generation photo-sensitizer applied at the wavelength of 630 nm to 660 nm, such as 'Chlorin e6' is injected into the vein, a portion of the body is incised as shown by reference numeral 402 of FIG. 4 after a predetermined time has passed, and then the apparatus is inserted into a target tissue 1 (solid cancer, etc.) in the body as shown by reference numerals 401 and 403 of FIG. 4 through a laparoscope (diameter: 15 mm or less) and an ultrasonic endoscope (diameter: 2.7 mm or less).

The capsule body 10 includes a capsule body 11, a double packing 12, a cap coupler 16, and an anchor 17.

Although the capsule body 11 may be formed in the shape of a cylinder, a square column, or a polygonal column, the capsule body may preferably have the shape of the cylinder.

As illustrated in FIG. 2, the capsule body 11 may include a space 18 formed as an empty space therein, and the battery 50 may be inserted into the space 18.

The cap coupler 16 is provided on an upper portion of the capsule body 11 to couple the silicone dome 40 to the upper portion. Although the coupling method of the silicone dome 40 may include gluing, tapping, molding and the like, molding is preferable.

The double packing 12 includes a packing body 15 that extends from the cap coupler 16 to have an inner radius smaller than the cap coupler 16, a first protrusion 13 that protrudes along the outer circumference of the packing body 15, and a second protrusion 14 that is spaced apart from the first protrusion 13 by a predetermined distance and protrudes along the outer circumference of the packing body 15.

The anchor 17 protrudes outwards below the cap coupler 16 of the capsule body 11, and is pointed at an end thereof to be fixedly inserted into the target tissue.

At least one anchor 17 may be provided and arranged to form an oblique line with the capsule body 11 so as not to be separated from the target tissue. It is preferable that an angle between the anchor and the capsule body 11 is within 60°.

The anchor 17 may be formed to have a straight shape, an "L" shape, and the like.

The board unit 20 is coupled to an inside of an upper portion of the space 18 of the capsule body 11, and is electrically connected to the battery 50 inserted into the space 18.

The board unit 20 includes a communication module (not shown) that performs human body communication, a control module (not shown) and the like. The communication module and the control module may be operated by power applied from the battery 50. In the state where the capsule type photodynamic therapy apparatus 100 is inserted into the body, the communication module and the control module may optionally perform a targeted photodynamic therapy several times through in vivo communication. Furthermore, the control module may be preferably configured to adjust light output or the like under external control. A method using galvanic coupling may be applied as the in vivo communication. This is because communication using the RF signal has a limit due to a high loss due to moisture in a human body, a dielectric constant of a medium is changed according to a path of a transmission signal in the human body depending on a location of an external signal transmitter, and accordingly channel characteristics are varied, so that it is difficult to predict the quality of the signal propagated to a receiver.

Furthermore, the communication module of the present invention may concentrate transmission signal energy wherever a receiving module is in a three dimensional space even in a homogeneous medium channel by applying a Coherently-incoherent Beamforming (CIB) method using phase encoding in place of frequency encoding that is a traditional encoding method of a multiple antenna.

The light irradiation unit 30 includes a flexible film 31, a board connector 32, and a micro-light source (uLED) 33.

The flexible film 31 is a film that is bendable as the term suggests, and is formed long in a rectangular shape, with a circuit pattern being printed thereon. The circuit pattern may have a terminal (electrode) to which at least two micro-light sources 33 are to be connected, and a terminal to which the board connector 32 is to be connected.

The circuit pattern(s) may be printed on only one surface or both surfaces of the flexible film 31. That is, the micro-light source(s) 33 may be provided on only one surface or both surfaces of the flexible film 31.

The flexible film 31 may be electrically connected to the upper portion of the board unit 20 to be formed long in the longitudinal direction of the capsule type photodynamic therapy apparatus 100.

The flexible film 31 may be formed to be bent in an inverted U shape as illustrated in FIGS. 1 to 3. In this case, it is preferable that at least two micro-light sources 33 are provided on only one surface of the film.

Furthermore, as illustrated in FIGS. 1 to 3, the micro-light source 33 may be located at a bent vertex of the flexible film 31. In this case, light may be radiated upwards and in both directions.

The flexible film 31 may be formed in a cylindrical shape by rolling like a column, and may be formed such that the board connector 32 is provided on an end of a side of the cylinder.

The board connector 32 may be provided on only an end of a side of the flexible film 31. In the case where the film is bent as shown in FIGS. 1 and 2, board connectors 32 may be provided on ends of both sides of the film to be electrically connected to the board unit 20, and may be operated under the control of the control module of the board unit 20.

At least two micro-light sources 33 may be provided to radiate light having a wavelength corresponding to 630 nm to 660 nm of the second-generation photo-sensitizer. Each micro-light source 33 may be preferably designed as a vertical or flip-chip structure which has a size of 100 um*60 um or less and a thickness of 10 um or less and in which the size of the electrode (terminal) provided on the flexible film 31 is 30 um*60 um and a distance between electrodes is 40 um for the electrical connection.

The silicone dome 40 includes a cap body 41 and a double packing coupler 42, and has the shape of a cap that is opened at a side thereof to transmit light radiated from the micro-light source 33 of the light irradiation unit 30 and to cover the light irradiation unit 30 and the board unit 20.

The silicone dome 40 is coupled to the upper portion of the capsule body 16 while covering the light irradiation unit 30 and the board unit 20. It is preferable that the silicone dome is molded with the capsule body 16 as described above.

The cap body 41 has the shape of the cap that is opened at a side thereof to transmit light irradiated from the micro-light source 33 of the light irradiation unit 30 and to cover the light irradiation unit 30 and the board unit 20.

The double packing coupler 42 is doubly coupled with the first protrusion 13 and the second protrusion 14 of the double packing 12 to doubly package the light irradiation unit 30 and the board unit 20 and thereby seal the light irradiation unit 30, the board unit 20, and the battery 50.

By way of example, the battery 50 may be formed of a Ti material in the shape of a pin, and supplies power to the board unit 20 and the light irradiation unit 30.

To be more specific, a packaging material of the battery that is a power supply of a capsule for laparoscope preferably applies suitable titanium (Ti) and titanium alloy (Ti-6Al-4V), which are biomaterials primarily used for medical purposes because they have high strength characteristics, low elastic modulus, very excellent processability, and excellent corrosion resistance.

The battery 50 may be formed in a plate shape or a shape corresponding to that of the capsule body 11.

The capsule type photodynamic therapy apparatus 100 having the above-described configuration may be configured to have power consumption as shown in Table 1 according to the size of the target tissue.

TABLE 1

| | Peritoneal carcinoma (diameter 1.5 Cm) | Digestive cancer (diameter 2.7 mm) |
|---|---|---|
| Single uLED size | 300*200 um | 160*110 um |
| Single uLED rating | 2.5 V, 3.5 mA (8.75 mW input) | 2.5 V, 1.5 mA (3.75 mW input) |
| Single uLED light output | 7 mW (efficiency 80% standard) | 3 mW (efficiency 80% standard) |
| Light-source arrangement | Parallel 3ea | Parallel 3ea |
| Total power consumption | 26 mW | 11.25 mW |
| Total light output | 21 mW (efficiency 80% standard) | 9 mW (efficiency 80% standard) |
| Other control and communication module power | 10 mW | 5 mW |
| Micro-light source module power consumption | 36 mW/90 min = 24 mWh 120 mWh in 5 procedures | 16.25 mW/90 min = 10.83 mW 54 mWh in 5 procedures |

Although the present invention was described with reference to specific embodiments shown in the drawings, it is apparent to those skilled in the art that the present invention may be changed and modified in various ways without departing from the scope of the present invention, which is described in the following claims.

What is claimed is:

1. A capsule type photodynamic therapy apparatus with an anchor, the apparatus comprising:
   a capsule body having the anchor that protrudes outwards to be anchored to a target tissue in a body;
   a board unit coupled to an inside of an upper portion along a longitudinal direction of the capsule body;
   a light irradiation unit electrically coupled to an upper portion of the board unit to be formed along a direction aligned with the longitudinal direction of the capsule body, radiating light in opposite directions perpendicular to the longitudinal direction of the capsule body, and including at least one micro-light source provided along the direction aligned with the longitudinal direction of the capsule body; and
   a silicone dome transmitting light radiated from the light irradiation unit, configured to have a shape of a cap that is opened at a side thereof to cover the light irradiation unit and the board unit, and coupled to the upper portion of the capsule body while covering the light irradiation unit and the board unit, thus packaging the capsule body, the light irradiation unit, and the board unit;
   wherein the capsule body comprises:
      a cylindrical capsule body;
      a cap coupler provided on the upper portion of the capsule body so that the silicone dome is coupled to the upper portion;
      a double packing extending from the cap coupler to have an inner radius smaller than that of the cap coupler, with a protrusion being two protrusions formed along an outer circumference thereof; and
      at least one anchor protruding outwards below the cap coupler of the capsule body, and pointed at an end thereof to be fixedly inserted into the target tissue, and
   wherein the silicone dome comprises:
      a cap body transmitting light irradiated from the light irradiation unit, configured to have the shape of the cap that is opened at a side thereof to cover the light irradiation unit and the board unit, and coupled to the upper portion of the capsule body while covering the light irradiation unit and the board unit; and
      a double packing coupler provided in the cap body corresponding to the double packing, and doubly coupled with the double packing to doubly package the light irradiation unit and the board unit.

2. The capsule type photodynamic therapy apparatus of claim 1, wherein the anchor protrudes to form an oblique line with an outer circumference of the capsule body within a predetermined angle.

3. The capsule type photodynamic therapy apparatus of claim 1, wherein the light irradiation unit comprises:
   at least two micro-light sources provided to radiate light;
   a flexible film formed along the direction aligned with the longitudinal direction of the capsule body, each of the micro-light sources being longitudinally connected to the flexible film to radiate light in the opposite directions perpendicular to the longitudinal direction of the capsule body; and
   a board connector provided on an end of the flexible film, connected electrically to the micro-light source, and coupled electrically to an upper portion of the board unit.

4. The capsule type photodynamic therapy apparatus of claim 3, wherein the flexible film comprises the micro-light sources on only one of two sides of the flexible film, and the flexible film is bent in an inverted U shape so that the micro-light sources radiate light in the opposite directions perpendicular to the longitudinal direction of the capsule body, and the board connector is provided on each of two ends of the flexible film.

5. The capsule type photodynamic therapy apparatus of claim 3, wherein the flexible film comprises at least three micro-light sources on only one of two sides of the flexible film, and the flexible film is bent in an inverted U shape so that the micro-light sources radiate light in the opposite directions perpendicular to the longitudinal direction of the capsule body and in a direction perpendicular to the opposite directions, and
   the board connector is provided on each of two ends of the bent flexible film.

6. The capsule type photodynamic therapy apparatus of claim 1, wherein the capsule body further comprises:
   a space defining an empty space therein; and
   a battery inserted into the space, and connected electrically to the board unit to supply power to the board unit and the light irradiation unit.

* * * * *